United States Patent [19]

Gibson et al.

[11] Patent Number: 4,847,418
[45] Date of Patent: * Jul. 11, 1989

[54] CONTINUOUS PROCESS FOR PREPARING ALKANOLAMINES

[75] Inventors: Charles A. Gibson; Moinuddin Ahmed; James R. Nelson, all of South Charleston, W. Va.

[73] Assignee: Union Carbide Corporation, Danbury, Conn.

[*] Notice: The portion of the term of this patent subsequent to Jul. 4, 2006 has been disclaimed.

[21] Appl. No.: 196,802

[22] Filed: May 16, 1988

Related U.S. Application Data

[63] Continuation of Ser. No. 561,046, Dec. 13, 1983, abandoned, Continuation-in-part of Ser. No. 259,899, May 4, 1981, abandoned.

[51] Int. Cl.$^4$ .................. C07C 85/00; C07C 85/02; C07C 89/00; C07C 89/02
[52] U.S. Cl. ................................. 564/477; 564/475
[58] Field of Search ........................ 564/475, 477

[56] References Cited

U.S. PATENT DOCUMENTS

| | | | |
|---|---|---|---|
| 1,904,013 | 8/1927 | Reid et al. | 260/584 |
| 2,196,554 | 5/1940 | Guinot | 260/584 |
| 2,373,199 | 4/1942 | Schwoegler et al. | 260/584 |
| 2,622,099 | 9/1948 | Ferroro et al. | 260/584 |
| 3,151,166 | 9/1964 | Milligan | 260/584 |
| 3,152,188 | 10/1964 | Kirkpatrick et al. | 260/477 |
| 3,544,632 | 12/1970 | Haarer et al. | 260/563 |
| 3,697,598 | 10/1972 | Weibull | 260/584 |
| 3,723,530 | 3/1973 | Goetze et al. | 260/584 |

FOREIGN PATENT DOCUMENTS 513508 10/1939 United Kingdom ............... 564/479

OTHER PUBLICATIONS

Batten, Chemical Abstracts, vol. 73, #36865g (1970).

Primary Examiner—Floyd D. Higel
Attorney, Agent, or Firm—Gerald L. Coon

[57] ABSTRACT

A continuous process is provided for preparing alkanolamines having a high yield of monoalkanolamine, which comprises continuously reacting a flowing stream of a homogeneous mixture of an alkylene oxide having from two to four carbon atoms and ammonia in a molar ratio of ammonia to alkylene oxide within the range from about 15:1 to about 50:1 at temperatures above the critical temperature of the mixture and at pressures above the critical pressure of the mixture and maintaining the mixture in a single phase having a density of at least 15 lbs./cu.ft. for the time necessary to form an alkanolamine product mixture containing at least about 65% by weight monoalkanolamine.

13 Claims, 1 Drawing Sheet

CONTINUOUS PROCESS FOR PREPARING ALKANOLAMINES

This application is a Continuation of prior U.S. application Ser. No. 561,046 Filing Date Dec. 13, 1983, now abandoned, and which is a continuation-in-part of application Ser. No. 259,899, Filing Date May 4, 1981, now abandoned.

BACKGROUND OF THE INVENTION

This invention relates to a process for the preparation of alkanolamines and, more particularly, to a continuous process for preparing alkanolamines with high yields of monoalkanolamine by the reaction of alkylene oxides with a large excess of ammonia wherein the reaction mixture is maintained in a single supercritical phase.

It is known that alkanolamines, which are used in a variety of commercial applications such as emulsification agents for soaps and cosmetics and as starting materials for the production of raw materials for detergents, wetting agents, emulsifiers, textile auxiliaries and the like, can be obtained by the reaction of alkylene oxides with ammonia or amines, the yield of alkanolamines being a mixture of mono, di-, and trialkanolamines with generally equal relative proportions of the three alkanolamines being frequently obtained. The relative proportions of these three alkanolamines in the product mixture, however, are known to depend on the relative quantities of alkylene oxide and ammonia that are reacted and processes have heretofore been used or suggested for achieving higher yields of one or more of the alkanolamines in the mixture which involve varying the proportion of such reactants, such as increasing the amount of ammonia relative to the alkylene oxide to obtain increased yields of monoalkanolamine, as well as by other process changes.

There is disclosed, for example, in U.S. Pat. No. 2,196,554 to H. M. Guinot a process for preparing mono-hydroxylalkylamines with yields of 90%–95% by reacting at least 30 parts by weight of ammonia with one part of alkylene oxide in a liquid phase reaction. Relatively dilute aqueous ammonia solutions are employed and the patent discloses that steam generated during concentration of the reaction product mixture is used for heating subsequent reaction product mixtures to separate ammonia gas therefrom, thus reducing the heat energy requiremtnts for the process.

Another process for preparing alkanolamines with extremely high yields of monoalkanolamines and only small amounts of the di- and trialkanolamines by reacting alkylene oxide with large excess amounts of ammonia in a liquid phase reaction system is disclosed in U.S. Pat. No. 3,697,598 to Weibull et al. The molar ratio of ammonia relative to alkylene oxide used in the process is within the range of 10:1 to 80:1 and the reaction is carried out in the presence of a cation exchange resin catalyst. The process of the patent is described as being a continuous process which is capable of being run isothermally or, preferably, adiabatically at temperatures in the range of from 20° C. to 250° C. when pressures are employed that are high enough to keep the reactants and reaction products in the liquid phase throughout the reaction. There is, however, no disclosure either in the description or in the examples of the patent which suggests that high yields of alkanolamines of any type are obtained when the process is carried out either adiabatically or isothermally without the use of cation exchange resin catalysts, and patentees state that without a cation exchange catalyst it is not possible to realize an adiabatic reaction because it is too slow.

Further, in U.S. Pat. No. 3,723,530 to Goetze et al., there is also disclosed a process for preparing a mixture of alkanolamines by the liquid phase reaction of ethylene oxide and a large excess of ammonia, that is, mole ratios of ammonia to ethylene oxide of from 14 to 40 to one. The patent teaches that when the reaction is carried out in the presence of up to 1 mole of diethanolamine per mole of ethylene oxide, the product obtained will be a mixture of only monoethanolamine and triethanolamine with little or no diethanolamine being present. The process of the patent is described as being capable of being run continuously, either isothermally or adiabatically. When operated continuously, the reaction is carried out in the liquid phase at temperatures in the range of from 60° C. to 150° C. and pressures of from 20 to 120 atmospheres, and the monoethanolamine content of the product mixture generally does not exceed 70 percent by weight. A continuous embodiment of the process which is described as being preferred is directed to initially reacting ethylene oxide with an excess of ammonia in a liquid phase to prepare a mixture of alkanolamines from which diethanolamine is separated and recycled. The recycled diethanolamine, when added to fresh ammonia and ethylene oxide starting reactants in the proportions described, results in the net formation of reduced amounts of diethanolamine. This process, however, requires the continuous separation of diethanolamine from the product mixture and is operated in the liquid phase.

In copending application Ser. No. 195,395, filed May 12, 1988, which is a continuation of application Ser. No. 561,045, filed Dec. 13, 1983, now abandoned, and which is a continuation-in-part of application Ser. No. 247061, filed Mar. 24, 1981, now abandoned, there is disclosed a process for preparing alkanolamines with high yields of monoalkanolamines by reacting alkylene oxide with a large excess of ammonia in a single supercritical phase. The process disclosed therein is described as being capable of running batchwise or continuously under isothermal or adiabatic conditions. When the process is run continuously, a reactor which is capable of operating as efficiently as possible as a "plug-flow" reactor may be employed for carrying out the reaction. The present invention is directed to preferred embodiments of the continuously run process described in said copending application.

SUMMARY OF THE INVENTION

In accordance with the present invention, there is provided a continuous process for preparing alkanolamines with high yields of monoalkanolamine which comprises continuously reacting in a plug-flow reactor a flowing stream of a homogeneous mixtrue of an alkylene oxide having from two to four carbon atoms and ammonia in a molar ratio of ammonia to alkylene oxide within the range from about 15:1 to about 50:1 at temperatures above the critical temperature of the mixture and at pressures above the critical pressure of the mixture and maintaining the mixture in a single phase having a density of at least about 15 lbs/cu.ft. (240 kg/cu.m.) for the time necessary to form an alkanolamine product mixture containing at least about 65% by weight monoalkanolamine. Unreacted ammonia may be separated from the product mixture and recycled while the alkanolamine product mixture is recovered, or the product mixture may be used in the preparation of further amine products, if desired.

The temperatures employed for carrying out the reaction are preferably as high as possible so that the reaction will proceed at a suitable rate and temperatures above the critical temperature of the reaction mixture are used. The pressure should be high enough to maintain the reaction mixture in a single homogeneous supercritical phase at any point during the reaction. The density of the supercritical reaction mixture is an important consideration as to the rate at which the reaction proceeds and should be maintained as high as possible throughout the reaction and generally at least about 15 lbs./cu.ft. The reaction can be carried out under isothermal, or preferably adiabatic, conditions and, while no catalyst is required, the presence of a small amount of water in the reaction mixture has an advantageous catalytic effect.

The term "supercritical phase," as used herein, is defined as the physical state of the reaction mixture wherein both the temperature and pressure conditions are above the critical values therefor in the reaction mixture. The term "plug-flow reactor," as used herein, is defined as a reactor in which there is essentially no back-mixing in a stream of fluids in the direction of the flow thereof through the reactor. Such plug-flow reactors may be non-adiabatic tubular or adiabatic pipe.

DETAILED DESCRIPTION OF THE INVENTION

The process of the invention comprises continuously reaction a homogeneous flowing stream of a mixture of alkylene oxide having from two to four carbon atoms and ammonia in a molar ratio of ammonia to alkylene oxide within the range from about 15:1 to about 50:1 at temperatures above the critical temperature of the mixture and at pressures above the critical pressure of the mixture and maintaining the mixture in a single, homogeneous supercritical phase. The pressure is maintained sufficiently high to produce a density of at least about 15 lbs/cu.ft. for the time necessary to form a product mixture composed at least about 65% by weight of monoalkanolamine (generally about 75%) and relatively small amounts of di-and trialkanolamine. If desired, unreacted ammonia can be separated from said product mixture at the completion of the reaction with alkylene oxide and recycled while the alkanolamine product mixture is recovered. The mono-, di-, and trialkanolamines can also be separated, if desired. The product mixture, including unreacted ammonia, may also be used in the preparation of other amine products.

The alkylene oxides to which the process of the present invention is applicable are any alkylene oxides having from two to four carbon atoms, including ethylene oxide, propylene oxide, 1,2-butylene oxide, 2,3-butylene oxide, and isobutylene oxide.

In accordance with the present invention, it is essential that a large excess of ammonia relative to the alkylene oxide is used in the reaction to obtain yields of monoalkanolamines of at least about 65 weight percent. It is advantageous to use from about 15 to about 50 moles, and preferably from about 20 to about 35 moles, of ammonia for each mole of alkylene oxide to obtain yields of monoalkanolamine in many cases of from about 70 to 85 weight percent.

It is essential that the reaction of alkylene oxide and ammonia be carried out in a homogeneous, single supercritical phase. The reaction can be carried out under isothermal or, preferably, adiabatic conditions; it is a particular advantage of this invention that no separate catalyst is needed for adiabatic operation. The temperature at which the reaction should be carried out is within the range from the critical temperature of the reaction mixture to about 200° C., though the upper limit of the temperature is not crucial. Preferably, the reaction temperature is within the range from the critical temperature of the reaction mixture (generally from about 130° C.) to about 180° C. The critical temperature is selected as the minimum temperature since that is about the temperature at which the reaction proceeds sufficiently rapidly to be commercially advantageous. Under isothermal conditions, since the reaction is strongly exothermic, it is necessary to withdraw heat from the reaction mixture to keep the temperature approximately constant.

In the case when the reaction is to be carried out under adiabatic or nearly adiabatic conditions, the reactants are preheated, preferably to a temperature in the range from about 100° C. to about 160° C., before they are introduced into the reactor. Because of the reaction heat involved, any selected initial reaction temperature rapidly increases and the initial reaction temperatures should be chosen so that the maximum desired temperature will be obtained during the period of residence of the reaction mixture within the reactor. The preferred maximum temperature is between about 170° C. and 180° C., though the higher the reaction temperature, the higher the pressure that is necessary to maintain the density of the reaction mixture as high as possible.

At such reaction temperatures, it is essential that the pressures imposed on the system are high enough to maintain the reaction mixture in a single supercritical phase. In any case, the reaction pressure should be at least as high as the critical pressure of the reaction mixture at any point encountered during the process. Preferably, the pressures imposed on the system are within the range from about 170° to about 240° atmospheres. The latter is a practical upper limit and is not crucial.

As pointed out hereinabove, the reaction mixture should be maintained at supercritical conditions to ensure that only one phase is present at sufficiently high temperatures and densities to permit the reaction to proceed at a suitable rate. The possible existence of two phases (vapor and liquid) at subcritical conditions is disadvantageous because (1) the ratios of ammonia and alkylene oxide will not be equivalent in the two phases due to their differences in volatilities, and (2) the low density vapor phase takes up valuable space in the reactor. The first disadvantage manifests itself by reducing the percent monoalkanolamine formed, because the liquid phase, where the vast majority of the reaction takes place, has been somewhat depleted of ammonia. Therefore, the effective ammonia to alkylene oxide mole ratio has been reduced.

The density of the reaction mixture should be maintained above the critical density (i.e., the density at the critical temperature and critical pressure) and, in general, should be at least about 15 lbs/cu.ft. (240 kg/cu.m). Preferably, the density of the reaction mixture should be maintained in the range of from about 21 to about 28 lbs/cu.ft. or even higher if practical, to enhance reaction rates. (Reaction rates are proportional to the density raised to the third power). Among the process variables, pressure has the most important influence on density, and operating at supercritical pressures is required to attain these desired densities, at the desired reaction temperatures. The mole ratio of ammonia and alkylene oxide reactants, and temperature also impact upon the density of the reaction mixture.

While it is not essential that the process of the invention be carried out in the presence of any catalyst, advantageous embodiments of the process of the invention may be carried out with a small amount of water incorporated in the reaction mixture along with the alkylene oxide and ammonia reactants. It has been found that the presence of small amounts of water in the reaction mixture has an advantageous catalytic effect on the reaction rate for forming alkanolamines, though it does not appear to affect the yield of monoalkanolamine in the product mixture. The amount of water that is present is not crucial, and only small amounts of water will achieve the catalytic affect that may be desired. In general, from about 0.5 percent to about 5 percent by weight of water, based on the weight of the reaction mixture, may be present. Amounts of water greatly in excess of that which may be catalytically useful, however, should be avoided to limit the energy requirements needed to separate water from the product mixture.

In accordance with the present invention, the process may be carried out continuously under isothermal or, preferably, adiabatic conditions in a plug-flow reactor or series of reactors which have a small cross-section in comparison to their length. A turbulent plug-flow reactor allows for the unidirectional flow of a process stream of reactants that minimizes back-mixing (axial mixing) within the reactor. The reactor may be provided with heat exchange means to maintain the temperature of the flowing reaction mixture at desired levels, but such temperature control means would not be needed if the reaction is carried out under adiabatic conditions.

In the continuous reaction process of the invention, a liquid mixture of the ammonia and alkylene oxide reactants in the molar ratios hereinabove described, preferably with a small amount of water admixed therewith, is preheated and then fed to the reactor through an inlet section therein where a swirling motion is imposed on the feed stream. When a tubular reactor (non-adiabatic) is employed, the reaction may be controlled to proceed within a relatively narrow temperature range such as, for example, about 20° C. though the temperature of the feed mixture may be varied over a wide temperature range, such as, for example, from about 20° to about 100° C. The process temperature will rapidly heat up to desired levels (the critical temperature of about 135° C. and above). Under adiabatic conditions, the mixture of reactants should be preheated to a temperature, from between about 100° C. to about 160° C., so that the maximum desired reaction temperature (generally from about 170° to 200°) will be attained during the period of residence of the reaction mixture within the reactor or series of reactors. The pressure within the reactor shall be high enough so that the reaction mixture is maintained in a single, homogeneous supercritical phase having the highest possible density at any point within the reactor.

The throughput rate of the reaction mixture should be chosen to provide a residence time within the reactor or reactors sufficient to permit the reaction to proceed to completion, generally less than about ½ hour. In an adiabatic reactor having the inlet feed configuration herein described, a flowing stream velocity of from about 0.15 to about 0.5 feet/second or even higher may be advantageously employed to permit plug-flow operation. At the completion of the reaction, that is, generally when all the alkylene oxide has been reacted, the unreacted ammonia can be separated from the product mixture by means known in the art, such as by reducing the pressure on the product mixture sufficiently to vaporize the ammonia so that it can be separated as a gas, or by distilling under pressure, and the alkanolamine product mixture may be recovered. The unreacted, separated ammonia can then be recycled, if desired, by repressurizing or condensing to a liquid state prior to mixing with fresh alkylene oxide. The alkanolamine analogues in the product mixture may also be separated by known distillation methods. The product mixture obtained during the continuous reaction process may also be used without further treatment as a starting material for the preparation of other organic amines.

The present invention will be further described with reference to the accompanying drawing in which.

Figure 1:
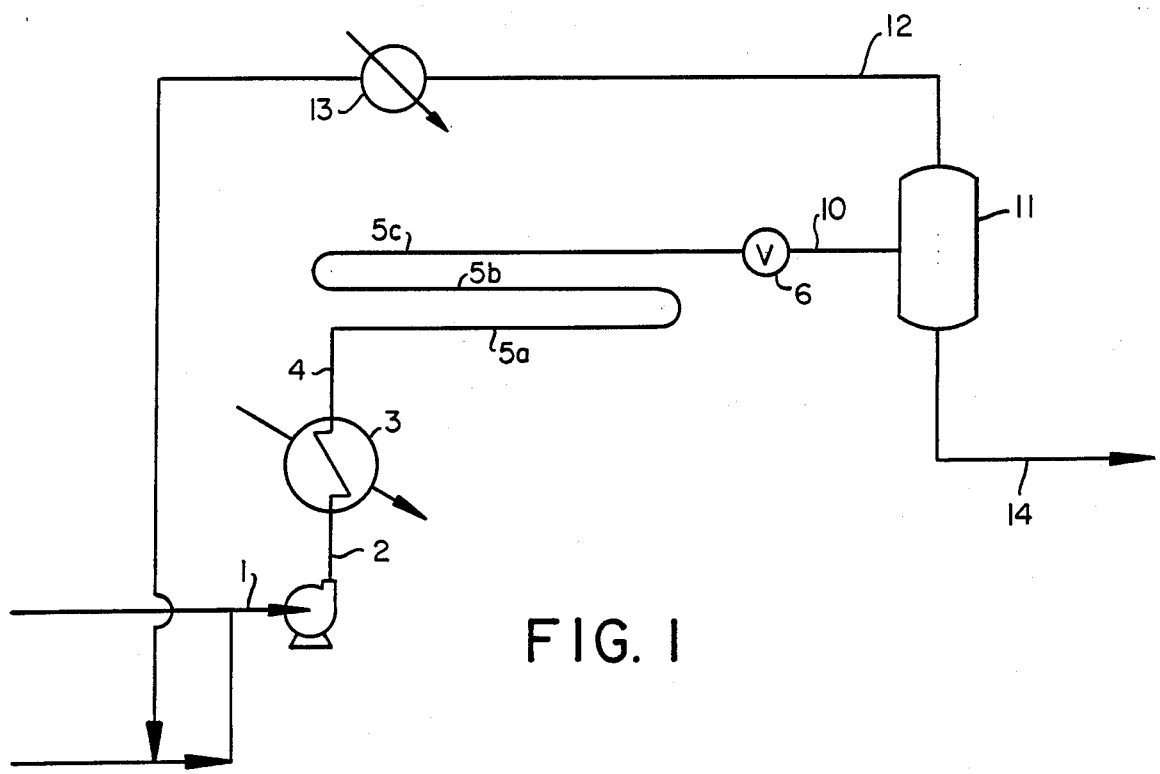
FIG. 1 is a schematic illustration of a typical adiabatic reaction system for use in the invention.

Referring to FIG. 1 of the drawing, liquid ammonia and alkylene oxide are blended in the proportions herein described in the feed pipe 1. Small amounts of water may also be added, if desired. The mixture of reactants is pumped through line 2 to a preheater 3 where the mixture is heated to a temperature in the range from about 100° C. to about 160° C. and then fed through an axial inlet pipe 4 to the adiabatic reactor. The adiabatic reactor may be a single plug-flow reactor or, as shown, a series of plug-flow reactor stages 5a, 5b, and 5c, each of which has an axial inlet pipe. Means are provided for imposing a swirling motion on the reaction mixture feed stream entering each reactor stage to minimize thermal stratification therein without increasing axial-mixing. The pressure within each of the reactor stages is maintained in the range, in general, from about 170° 240 atm by a pressure control valve 6 so that the reaction mixture stream is in a single phase at any point within the reactor and has a density of at least 15 lb/cu.ft..

The number of reactor stages employed may vary, depending on the amount of product to be produced, the total length of reactor required to achieve the desired production rate, the feasible length for any reactor stage, and similar considerations. A typical system may comprises from 1 to 6 reactor stages of up to 100 feet or more in length with 3 to 5 reactor stages being generally advantageously employed.

The product mixture in which all or substantially all of the alkylene oxide has been converted to alkanolamines is fed from the last adiabatic reactor stage 5c through pressure control valve 6 and line 10, where the product mixture stream is depressurized to between about atmospheric pressure and 40 atm, and then fed immediately into a flash separator 11. In the flash separator 11 a substantial amount of the unreacted ammonia rapidly separates from the product mixture as a gas which escapes at the top of the separator 11 in gaseous form and is recycled via line 12 through a compressor or condenser 13. The alkanolamine product mixture is drawn from the bottom of the separator 11 through line 14 for refining if desried.

Figure 2:
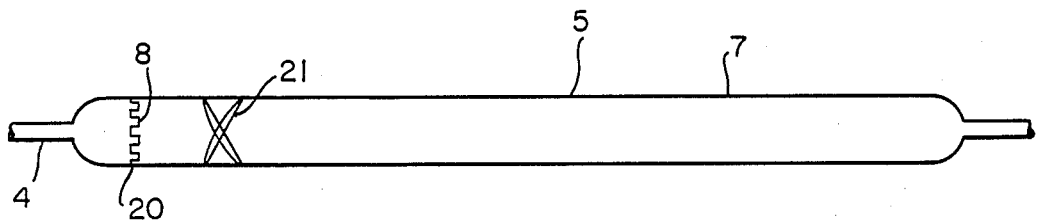
FIG. 2 is a schematic illustration of an adiabatic plug-flow reactor suitable for use in the invention.

FIG. 2 illustrates an adiabatic reactor 5 typical of the reactor stages 5a, 5b, or 5c of FIG. 1 having an axial inlet pipe 4 into a generally cylindrical hollow body 7 having a small cross-section in comparison to its length which defines an internal, longitudinally extending passageway. Mounted within the inlet end 20 thereof is a pair of opposed, semi-elliptically shaped baffles 21 which impose a swirling motion on the reaction mixture fed therethrough to achieve a swirling plug-flow regime for the reactor. Between the inlet pipe 4 and the opposed baffles 21 in the inlet end 20 of said reactor 5 is mounted a perforated plate 8 which serves to distribute and straighten the flow of fluid entering the cylindrical body 7 of said reactor 5. The semi-elliptically shaped baffles 21, which impose a swirling motion to the flowing stream of fluid within the reactor, may be prepared from semi-elliptic plates having ratios of major to minor axis of from about 1.25:1 to about 2.0:1. Other means for imposing a swirling motion to the flow of fluid through the reactor may also be used such as, for example, baffles with varying configuration, spacing, numbers, size, and method of mounting within the inlet end of the reactor, the cross-section and length of the reactor, the velocity of flow through the reactor and the like being factors which must be considered in choosing the particular configuration desired.

In a typical embodiment of the process of the invention, liquid ethylene oxide and ammonia in a molar ratio of ammonia to ethylene oxide of 30:1 are blended in feed pipe 1 along with 3 percent by weight of water. The mixture of reactants is pumped through line 2 to a preheater 3 where the mixture is heated to a temperature of about 130° C. and then fed to adiabatic plug-flow reactor stage 5a, a reactor having an outlet diameter of 30 inches and a length of 100 feet, at a velocity of 0.3 ft/sec. The reaction mixture is subsequently fed at such velocity to 3 successive adiabatic plug-flow reactor stages of similar dimensions and inlet configuration. The pressure in the reactor stages is controlled by pressure control valve, high enough to maintain the reactant mixtures in a single, homogeneous phase having a density of 24 lbs./cu.ft. at any point therein, generally about 200 to 210 atmospheres. After a total residence time in the reactor of about 25 to 30 minutes, the product mixture exits from the last reactor stage at a temperature of about 175° C. and is fed through pressure control valve 3 and line 10 to flash separator 11. The product mixture passing through line 10 is depressurized to about 20 atmospheres and when the product mixture enters the flash separator 11, unreacted ammonia is rapidly separated therefrom and exits from the top of the separator through line 12. The unreacted ammonia is then condensed to a liquid in condenser 13 and recycled.

The alkanolamine product mixture is fed from the bottom of separator 11 through line 14, refined by known distillation techniques and, recovered.

This invention will become more clear when considered together with the following examples which are set forth as being merely illustrative of the invention and which are not intended in any manner to be limitative thereof. Unless otherwise indicated, all parts and percentages are by weight.

EXAMPLE 1

A reaction system and apparatus similar to that shown in the drawings (FIG. 1 and FIG. 2) except that the adiabatic plug-flow reactor is comprised of 4 reactor stages, each of which is 30 inches in diameter and 100 feet long, was used in a continuous run in which ethylene oxide was reacted with ammonia. In this run a liquid ethylene oxide feed of 5000 pounds per hour was mixed with a liquid ammonia-water mixture feed of 90,000 pounds per hour (96 percent $NH_3$, 4 percent water) to give an ammonia to ethylene oxide mole ratio of 45:1. The mixed ammonia and ethylene oxide feed was preheated to a temperature of about 150° C. and then pumped into the first reactor stage at a velocity of about 0.27 feet/sec. The pressure in the reactor stages was controlled to maintain the flowing stream in a single phase having an average reaction mixture density of about 21.5 lbs/cu.ft. The pressure at the outlet of the final reactor stage was about 2700 psig (about 184 atm.) and the temperature of the product mixture at the outlet of the fourth reactor stage was about 170° C. after a residence time within the reactor stages of 28 minutes and the reaction mixture was in the supercritical phase. The product mixture from the final reactor stage was depressurized to about 400 psig (27 atm.) in the line leading to a flash-tank separator and substantially all the unreacted ammonia separated from the product mixture in the flash-tank separator. The separated ammonia from the top of the separator was passed through a condenser where it was condensed to a liquid and then was recycled.

The product mixture was recovered from the bottom of the flash-tank separator, refined to remove the small amount of unreacted, entrained ammonia, and then collected. The composition of the product mixture was determined by gas chromatographic analysis to contain 80 percent by weight of monoethanolamine, 17.5 percent by weight of diethanolamine, and 2.5 percent by weight of triethanolamine. No measurable amount of unreacted ethylene oxide was found.

EXAMPLE 2

Using the reaction system and apparatus of Example 1, a continous run was made in which a liquid ethylene oxide feed of 5200 pounds per hour was mixed with a liquid ammonia-water mixture feed of 90,000 pounds per hour (97 percent $NH_3$ and 3 percent water) to give an ammonial to ethylene oxide mole ratio of 44:1. The mixed ammonia and ethylene oxide feed was preheated to a temperature of about 154° C. and pumped into the first reactor stage at a velocity of about 0.26 ft./sec. The pressure in the reactor stages was controlled to maintain the flowing stream of reactants in a single phase having an average reaction mixture density of about 22.5 lbs./cu.ft. The pressure at the outlet of the final reactor stage was about 3000 psig (204 atms.) and the temperature of the product mixture at the outlet of the final reactor stage was about 174.5° C. after a residence time of 29 minutes, demonstrating that the reaction mixture had achieved supercritical conditions. The temperature of the reaction mixture at the outlet of each of the reactor stages was found to be:

at the outlet of the first reactor stage: 166° C.
at the outlet of the second reactor stage: 169.6° C.
at the outlet of the third reactor stage: 174.8° C.

The product mixture from the final reactor stage was depressurized to about 400 psig and fed to a flash-tank separator where substatially all the unreacted ammonia rapidly separated from the product mixture and was then taken from the top of the separator, condensed to a liquid and recycled.

The product mixture recovered from the bottom of the separator was collected and determined to have the following composition:

83 percent by weight monoethanolamine
15 percent by weight diethanolamine 2 percent by weight triethanolamine No measurable amount of unreacted ethylene oxide was found in the product mixture.

EXAMPLE 3

Using the reaction system and apparatus of Example 1, a continous run was made in which a liquid ethylene oxide feed of 10,000 pounds per hour was mixed with a liquid ammonia-water mixture feed of 114,000 pounds per hour (97.5 percent $NH_3$, 2.5 percent water) to give an ammonia to ethylene oxide mole ratio of 29:1. The reactant mixture was preheated to a temperature of about 150° C. and pumped into the first reactor stage at a velocity of 0.33 ft./sec. The pressure in the reactor stages was controlled to maintain the reactant mixture in a single phase having an average reaction mixture density of about 23 lbs./cu.ft.

The pressure at the outlet of the final reactor was about 3,000 psig (204 atms.) and the temperature of the product mixture at the outlet of the final reactor stage was about 180° C. after a residence time of 23 minutes, again showing that supercritical conditions had been reached.

Analysis of the product mixture after separating unreacted ammonia was determined to be:

76.2 percent by weight of monoethanolamine 20.8 percent by weight of diethanolamine 3.0 percent by weight of triethanolamine It was also determined that 0.1 percent unreacted ethylene oxide was present in the product mixture.

What is claimed is:

1. A continuous process for preparing alkanolamines with high yields of monoalkanolamines, which comprises continuously reacting in a plug flow reactor a stream of a homogeneous mixture of an alkylene oxide having from two to four carbon atoms and ammonia in a molar ratio of ammonia to alkylene oxide within the range from about 15:1 to about 50:1 at temperatures above the critical temperature of the mixture and at pressures above the critical pressure of the mixture and maintaining the mixture in a single phase having a density of at least about 15 lbs./cu.ft. for the time necessary to form an alkanolamine product mixture containing at least about 65% by weight monoalkanolamine, said stream flowing in said reactor in a manner that minimizes back-mixing.

2. The process of claim 1 wherein said homogeneous mixture of reactants also contains a small catalytic amount of water.

3. The process of claim 1 wherein a swirling motion is imposed on the stream of reactants flowing through said reactor to avoid thermal stratification.

4. The process of claim 1 wherein unreacted ammonia is separated from the alkanolamine product mixture after completion of the reaction of the alkylene oxide.

5. The process of claim 4 wherein said separated unreacted ammonia is liquified and recycled for reaction with fresh amounts of alkylene oxide.

6. The process of claim 2 wherein a swirling motion is imposed on the stream of reactants flowing through said reactor to avoid thermal statification.

7. The process of claim 1 wherein the reaction is carried out under adiabatic conditions at a temperature of up to about 200° C.

8. The process of claim 2 wherein the reaction is carried out under adiabatic conditions at temperatures of up to about 200° C.

9. The process of claim 6 wherein the reaction is carried out under adiabatic conditions.

10. The process of claim 1 wherein the reaction is carried out at pressures in the range from about 170 atmospheres to about 240 atmospheres.

11. The process of claim 6 wherein the reaction is carried out at pressures in the range from about 170 atmospheres to about 240 atmosphere.

12. The process of claim 9 wherein the reaction is carried out at pressures in the range from about 170 atmospheres to about 240 atmospheres.

13. A continuous process for preparing alkanolamines with high yields of monoalkanolamines which comprises continuously reacting in a plug flow reactor a stream of a homogeneous mixture of an alkylene oxide having from two to four carbon atoms and ammonia in a molar ratio of ammonia to alkylene oxide within the range from about 15:1 to about 50:1 maintained in a single supercritical fluid phase having a density of at least 15 lbs./cu.ft. for the time necessary to form an alkanolamine product mixture containing predominately monoalkanolamine, said stream flowing in said reactor in a manner that minimizes backmixing.

* * * * *